US00PP21922P2

(12) United States Plant Patent
Madsen

(10) Patent No.: US PP21,922 P2
(45) Date of Patent: May 17, 2011

(54) *CAMPANULA* PLANT NAMED 'PKMP07'

(50) Latin Name: *Campanula portenschlagiana*
Varietal Denomination: PKMP07

(75) Inventor: Christian Hald Madsen, Korsor (DK)

(73) Assignee: Gartneriet PKM A/S, Odense N (DK)

( * ) Notice: Subject to any disclaimer, the term of this patent is extended or adjusted under 35 U.S.C. 154(b) by 0 days.

(21) Appl. No.: 12/657,041

(22) Filed: Jan. 13, 2010

(51) Int. Cl.
*A01H 5/00* (2006.01)

(52) U.S. Cl. ..... Plt./414

(58) Field of Classification Search ..... Plt./414
See application file for complete search history.

*Primary Examiner* — Annette H Para
(74) *Attorney, Agent, or Firm* — Foley & Lardner LLP

(57) ABSTRACT

A new and distinct cultivar of *Campanula portenschlagiana* plant named 'PKMP07', characterized by having compact, upright plant habit; dense and bushy plant form mainly due to more upright stems; vigorous growth habit and no need for chemical growth retardation; greater number of flowers per plant, large upright violet flowers, no need for vernalization; and pollen-free.

6 Drawing Sheets

Latin name of the genus and species of the plant claimed: *Campanula portenschlagiana.*

Variety denomination: 'PKMP07'.

BACKGROUND OF THE INVENTION

The present invention relates to a new and distinct cultivar of *Campanula* plant, botanically known as *Campanula portenschlagiana* Schult., commonly known as Dalmatian Bellflower, and hereinafter referred to by the name 'PKMP07'.

The new *Campanula*, 'PKMP07', is a product of a planned breeding program conducted by the inventor, Christian Hald Madsen, in Søhus, Denmark. The objective of the breeding program is to develop a new pollen-free *Campanula* variety with uniform and compact plant form and deep purple flowers.

The new *Campanula* cultivar originated as a whole plant mutation, induced by irradiation of gamma rays of *Campanula portenschlagiana* Schult. 'PKMP05', (patented, U.S. Plant Pat. No. 17,188) in 2007 by the inventor. The inventor selected the new *Campanula* 'PKMP07' in 2008 on the basis of it being pollen-free.

Asexual reproduction of the new *Campanula* 'PKMP07' by terminal cuttings since March of 2008 in Søhus, Denmark, has shown that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be the unique characteristics of 'PKMP07'. These characteristics in combination distinguish 'PKMP07' as a new and distinct cultivar:

1. Upright plant habit;
2. Dense and bushy plant form, mainly due to more upright stems;
3. Vigorous growth habit, and less need for chemical growth retardation;
4. More uniform and deeper purple flower color;

5. No need for vernalization; and
6. Pollen-free.

Side-by-side comparisons between the new *Campanula* 'PKMP07' and the parental cultivar, *Campanula* 'PKMP05' (patented, U.S. Plant Pat. No. 17,188), were conducted by the inventor in Stige, Denmark. Plants of 'PKMP07' differ from the plants of 'PKMP05' in the unique characteristic of having no pollen.

Of the many commercial cultivars known to the inventor, the most similar in comparison to 'PKMP07' is the parental cultivar, *Campanula* 'PKMP05' (patented, U.S. Plant Pat. No. 17,188), as described above.

BRIEF DESCRIPTION OF THE PHOTOGRAPHS

The accompanying colored photographs illustrate the overall appearance of the new cultivar 'PKMP07', showing the colors as true as it is reasonably possible to obtain in colored reproductions of this type. Colors in the photographs may differ slightly from the color values cited in the detailed botanical description, which more accurately describe the actual colors of 'PKMP07'.

DETAILED BOTANICAL DESCRIPTION

Figure 1:
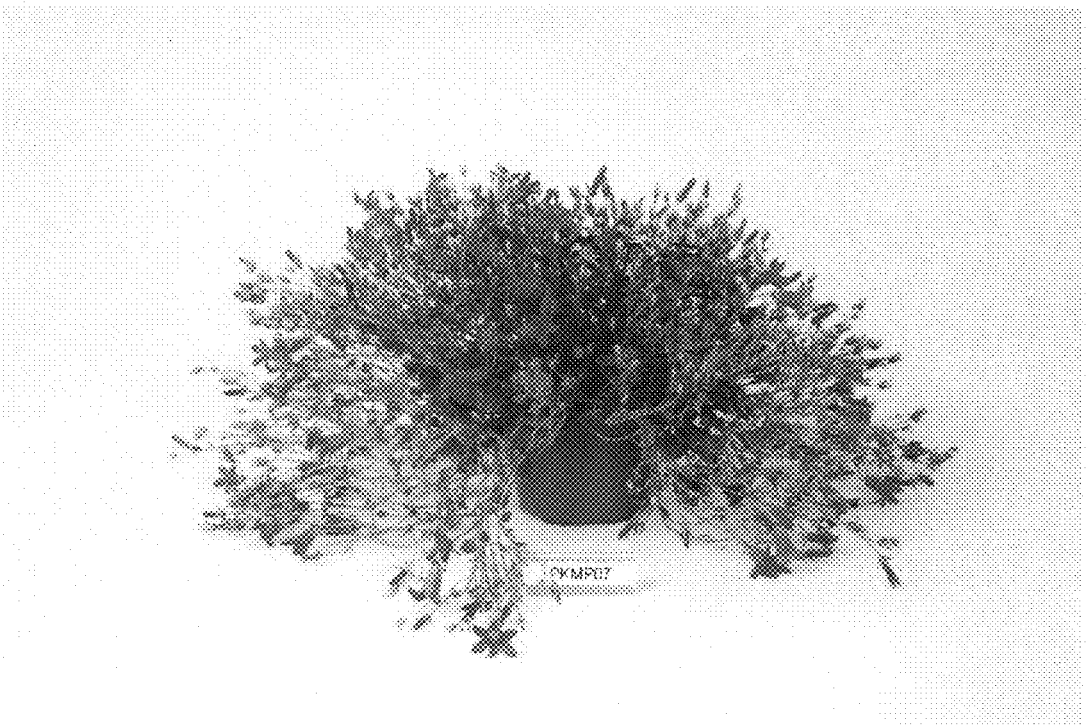
FIG. 1 shows a side perspective view of a typical flowering plant of 'PKMP07' as grown in a 10.5 cm pot.
Figure 2:
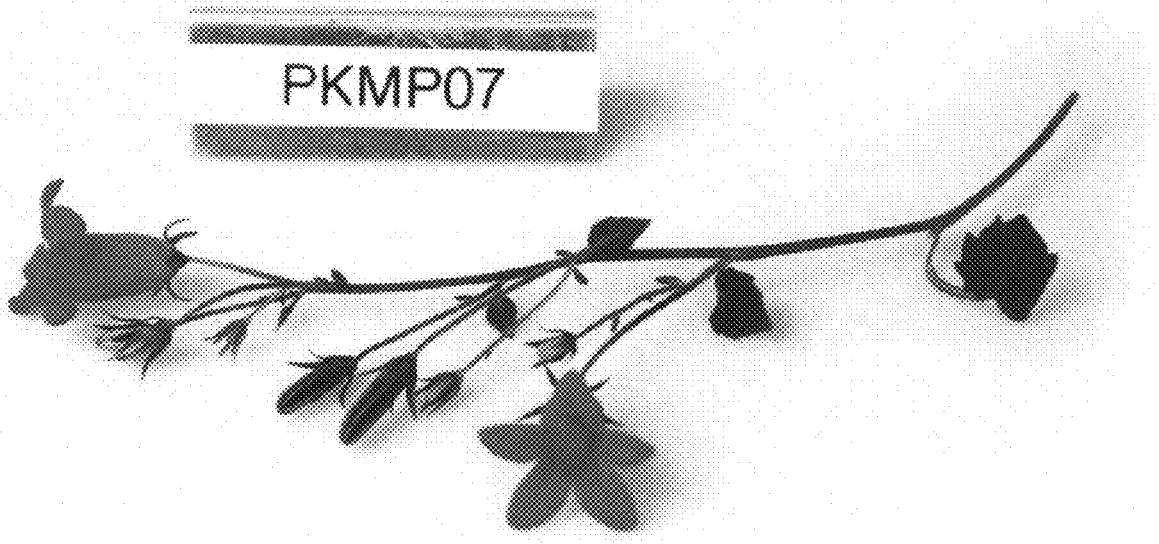
FIG. 2 shows a close-up view of typical flowering raceme of 'PKMP07'.
Figure 3:
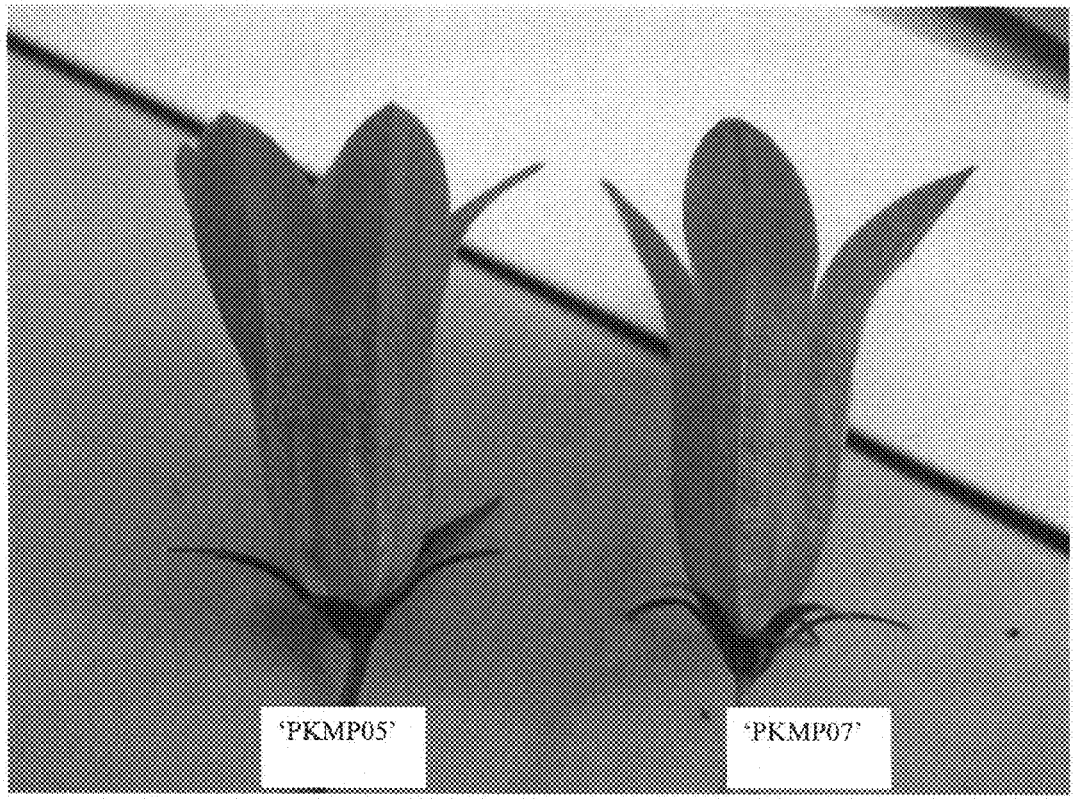
FIG. 3 shows a comparison view of a typical young flower of 'PKMP07' (on right) compared to a typical young flower of 'PKMP05' (on left).
Figure 4:
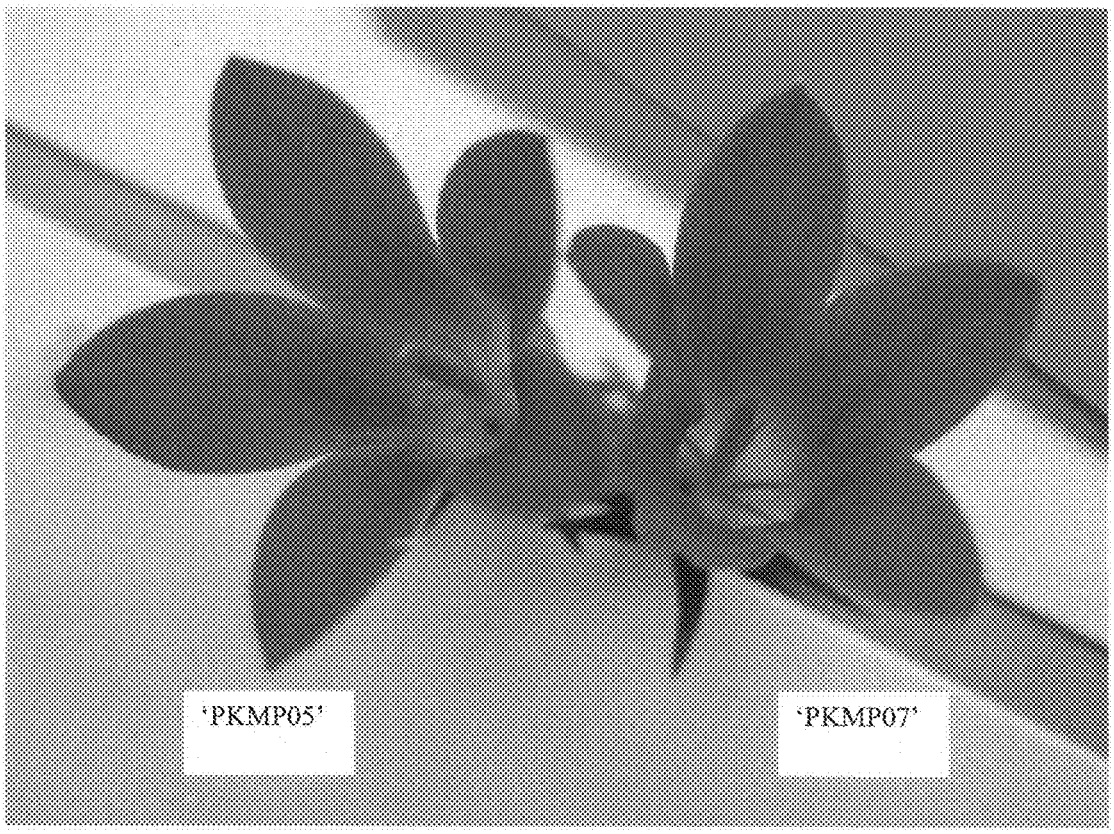
FIG. 4 shows a comparison view of a typical fully-opened flower of 'PKMP07' (on right) compared to a typical fully-opened flower of 'PKMP05' (on left).
Figure 5:
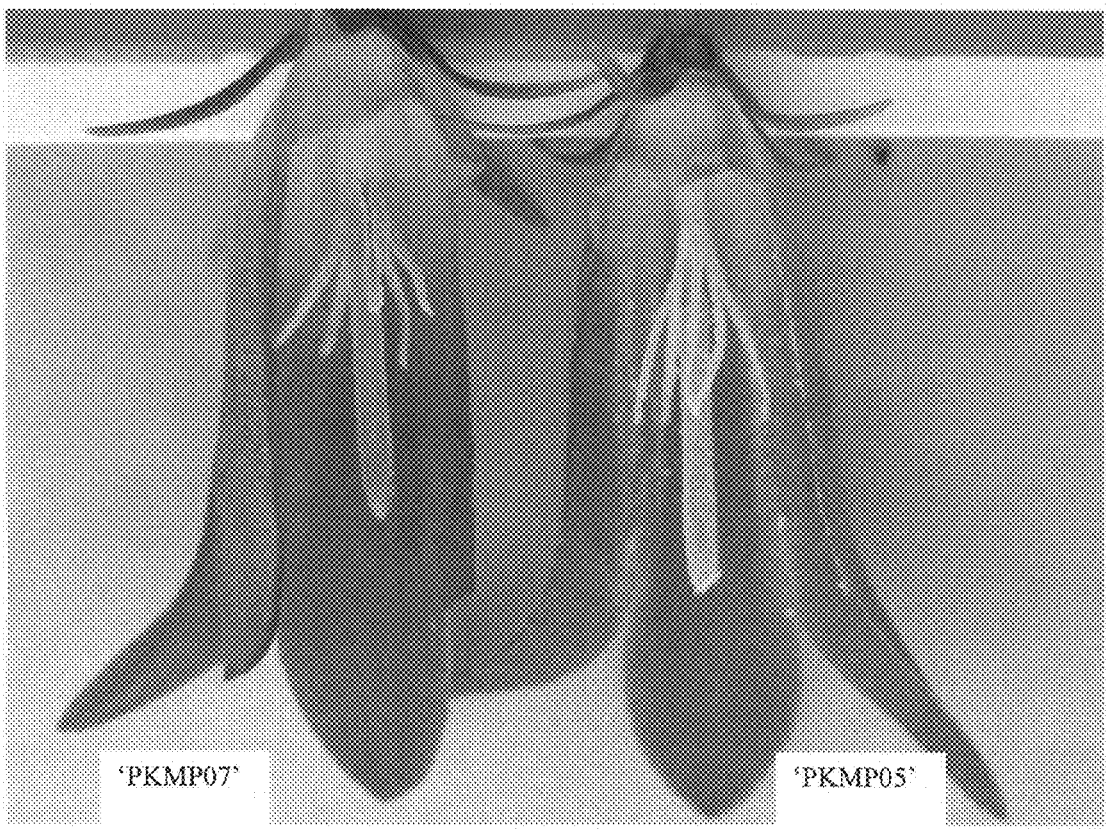
FIG. 5 shows a close-up comparison view of the pollen produced by a typical flower of 'PKMP05' (on right) and the absence of pollen produced by a typical flower of 'PKMP07' (on left).
Figure 6:
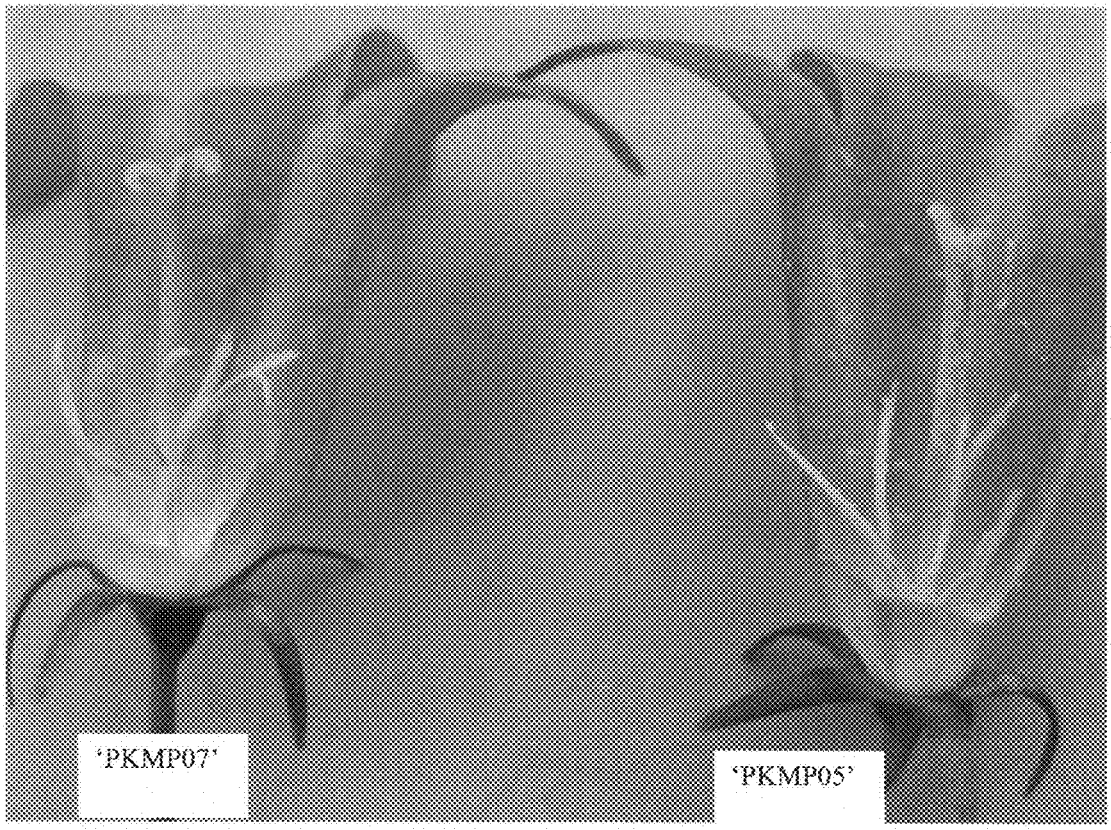
FIG. 6 shows a comparison view of a mature flower with unfolded style of 'PKMP07' (on left) compared to a mature flower with unfolded style of 'PKMP05' (on right).

The new *Campanula* 'PKMP07' has not been observed under all possible environmental conditions. The phenotype of the new cultivar may vary significantly with variations in environment such as temperature, light intensity, day length, and fertility level without any variance in genotype.

The aforementioned photographs, together with the following observations, measurements and values describe plants of the new *Campanula* 'PKMP07' as grown in a heated and lighted, glass-covered greenhouse in Søhus, Denmark, under conditions which closely approximate those generally used in commercial practice. Plants of 'PKMP07' are grown in a glass-covered greenhouse where day temperatures in the greenhouse range from 18-22° C. and the average night temperatures is 16° C. Light levels used while growing plants of 'PKMP07' are 100Wm$^2$. Plants of 'PKMP07' are grown with 16 to 18 hour long day photoperiodic treatments; 10 hour short day photoperiodic treatments for propagation and seedlings. No growth retardants were used when growing plants of the new *Campanula* 'PKMP07'.

The age of the 'PKMP07' plants described is 14 weeks old after cutting, as grown in 10.5 cm pots. The photographs and descriptions were taken during the winter season when day temperatures in the glass-covered greenhouse ranged from 18-22° C. and when the night average temperature in the glass-covered greenhouse was 16° C.

Color references are made to The Royal Horticultural Society Colour Chart (R.H.S.), 4$^{th}$ edition, except where general colors of ordinary significance are used.

Classification:

*Botanical.*—*Campanula portenschlagiana* Schult.

Parentage: *Campanula portenschlagiana* Schult. 'PKMP05' (patented, U.S. Plant Pat. No. 17,188)

Propagation:

*Type.*—Terminal vegetative cuttings.

*Time to initiate roots.*—About 10 to 14 days at 18 to 21° C. in tunnels in a greenhouse.

*Root description.*—Fine, well branched.

Plant:

*Form.*—Perennial, herbaceous, rosette plant with upright plant habit and overall globular shape. Campanulate flowers in racemes. Freely branching with lateral branches forming at every node; dense and bushy.

*Crop time.*—After rooting, about 14 weeks are required to produce finished flowering plants in 11 cm pots.

*Vigor.*—Vigorous.

*Size.*—Height (soil level to top of plant plane): About 13 cm. Spread (width): About 27 cm.

*Stem.*—Shape: Round. Strength: Stiff. Color: RHS 141B, green.

*Lateral branches.*—Quantity: About 85-90 per plant. Length (including flowers): About 10 cm. Diameter: About 1 mm to 2 mm. Aspect: Center of plant: ascending; Perimeter of plant: spreading to drooping. Texture: Hispidulous and white lactate. Color: RHS 141B, green. Basal branching: Yes, when flowering. Internode Length: About 25 mm.

Foliage:

*Quantity of leaves per lateral branch.*—About 5.

*Arrangement.*—Single, alternate.

*Length.*—Basal: About 15 mm to 20 mm; Apical: About 4 mm to 5 mm.

*Width.*—Basal: About 25 mm to 30 mm; Apical: About 2 mm to 3 mm.

*Shape.*—Cordate, dentate.

*Apex.*—Rounded.

*Base.*—Cordate.

*Margin.*—Broadly dentate.

*Texture.*—Smooth, glabrous, dull.

*Color.*—Upper surfaces (young and mature foliage) RHS N138A, green; Under surfaces (young and mature foliage): RHS 138A, green.

*Venation.*—Pattern: Palmate. Color: (Upper and under surfaces) RHS N138A, green.

*Petiole.*—Length: Basal: About 4 cm to 5 cm; Apical: Up to 1 cm. Diameter: 1 mm to 2 mm. Texture: Smooth, glabrous. Color: RHS N138B, green.

Inflorescence:

*Flower arrangement and shape.*—Single, upright flowers in racemes; acropetal, campanulate flowers with small star shaped calyx.

*Natural flowering season.*—Continuous throughout the spring and summer. Season can be extended by long day treatments, no vernalization needed.

*Flower longevity on the plant.*—About 5-9 days; however, longevity of individual flowers is highly dependent on temperature and light conditions. Flowers persistent.

*Fragrance.*—None.

*Inflorescence size.*—Length: About 8 cm. Diameter: About 23 cm.

*Quantity of flower buds and flowers per plant.*—About 1500.

*Quantity of flower buds per lateral stem.*—About 6.

*Quantity of flowers per lateral stem.*—About 9.

*Flowers.*—Depth: About 18 mm. Diameter: About 23 mm. Shape: Lanceolate, with acuminate lobes (about 7 mm long and 5 mm wide). Aspect: Upward to outward. Corolla color: RHS N87A, violet (upper surface), and RHS N88D, violet (under surface), and the bottom of the bell has this same violet color.

*Buds.*—Length: Up to 15 mm. Diameter: Up to 4 mm. Shape: Oblong, ridged. Color: RHS 143C, green with RHS 84A to RHS 84D, violet, on the edges.

*Petals.*—Arrangement: Single, sympetalous. Quantity per flower: 5. Overall shape: Bell-shaped, campanulate. Apex: Acute. Base: Fused. Length: About 8 mm to 10 mm. Width: About 7 mm. Margin: Entire. Texture: Velvety. Color (when opening): Upper surface: RHS N82A, purple-violet; Under surface RHS N82D, purple-violet. Color (when fully opened): Upper surface: RHS N87A, violet; Under surface RHS N88D, violet. Fading: None, but withers to RHS 156C, gray-white.

*Sepals.*—Arrangement: Free. Quantity per flower: 5. Overall shape: Arrow-shaped. Apex: Cuspidate. Base: Fused. Length: About 3 mm. Width: About 1 mm. Margin: Entire. Texture: Shiny, glabrous. Color: (immature — both surfaces): RHS 144B, yellow-green. Color: (mature — both surfaces): RHS 138A, green.

*Peduncle.*—Strength: Moderately strong. Length: About 30 mm. Diameter: About 1 mm. Color: RHS 141B, green.

Reproductive organs:

*Androecium.*—Stamen: Quantity per flower: 5; fused until pollen has been shed. Anther: Shape: Fused, after shedding curling. Length: About 1 mm. Color: RHS 158B, yellow-white. Pollen: None.

*Gynoecium.*—Pistil: Quantity per flower: 1. Length: About 12 mm. Stigma: Shape: Tripartite. Color: RHS 85A, violet. Style: Length: About 11 mm. Color: RHS 84B, violet. Ovary: Color: RHS 150D, yellow-green.

Seeds:

*Quantity.*—25 per flower.

*Length.*—About 1 mm.

*Diameter.*—About 0.3 mm.

*Texture.*—Smooth and glabrous.

*Color.*—Greyed-orange, RHS 175A.

Fruit:

*Type.*—Capsule.

*Length.*—About 6 mm to 8 mm.

*Diameter.*—About 2 mm to 3 mm.

*Color.*—RHS 164C, greyed-orange.

Growth retardants: No growth retardants were used in the breeding program.

Weather tolerance: Plants of the new *Campanula* have exhibited good tolerance to drought, rain and wind, with low temperature resistance to −20° C.

Disease/pest resistance: 'PKMP07' is not resistant to any diseases or pests typical to *Campanula* cultivars.

Disease/pest susceptibility: 'PKMP07' is not susceptible to *Botrytis*.

What is claimed is:

1. A new and distinct cultivar of *Campanula portenschlagiana* plant named 'PKMP07', as illustrated and described herein.

* * * * *